United States Patent
Posthuma (10) Patent No.: US 7,115,386 B2
(45) Date of Patent: Oct. 3, 2006

(54) DEVICE AND METHOD FOR CARRYING OUT IMMUNOLOGICAL MARKING TECHNIQUES FOR THIN-SECTIONED TISSUE

(75) Inventor: George Posthuma, Doorn (NL)

(73) Assignee: Leica Mikrosysteme GmbH, (AT)

(*) Notice: Subject to any disclaimer, the term of this patent is extended or adjusted under 35 U.S.C. 154(b) by 0 days.

(21) Appl. No.: 10/525,480

(22) PCT Filed: Jul. 16, 2003

(86) PCT No.: PCT/EP03/50309

§ 371 (c)(1),
(2), (4) Date: Feb. 24, 2005

(87) PCT Pub. No.: WO2004/025273

PCT Pub. Date: Mar. 25, 2004

(65) Prior Publication Data

US 2005/0233409 A1  Oct. 20, 2005

(30) Foreign Application Priority Data

Aug. 29, 2002 (DE) .................... 102 39 739

(51) Int. Cl.
G01N 1/30 (2006.01)
G01N 1/31 (2006.01)
G01N 35/02 (2006.01)

(52) U.S. Cl. .................. 435/40.52; 422/63; 422/65; 422/100; 422/102; 422/104; 435/40.5; 435/40.51; 435/287.3; 436/47; 436/49; 436/174; 436/180

(58) Field of Classification Search .... 435/40.5–40.52, 435/287.3, 63, 162; 436/63, 162, 178–180, 436/525, 526, 42, 47, 174, 176; 422/63, 422/65–67, 100, 102, 104
See application file for complete search history.

(56) References Cited

U.S. PATENT DOCUMENTS

| 3,350,220 A | * | 10/1967 | Isreeli | 427/2.13 |
| 3,363,468 A | * | 1/1968 | Blades | 73/864.51 |
| 3,762,879 A | * | 10/1973 | Moran | 422/65 |
| 3,976,028 A | | 8/1976 | Howells et al. | |
| 4,731,335 A | | 3/1988 | Brigati | |

(Continued)

FOREIGN PATENT DOCUMENTS

DE 29817912 U1 * 1/1999

(Continued)

OTHER PUBLICATIONS

Griffith et al., "A Reliable and Convenient Method to Store Ultrathin Thawed Cryosections Prior to Immunolabeling", 2002, The Journal of Histochemistry & Cytochemistry, vol. 50, pp. 57-62.*

Primary Examiner—Long V. Le
Assistant Examiner—Unsu Jung
(74) Attorney, Agent, or Firm—Simpson & Simpson, PLLC (57) ABSTRACT

The invention relates to a device and a method for carrying out in an optimized and automated manner immunological marking techniques for thin-sectioned tissue (2b). A support plate (1) which can be automatically moved by means of a computer-controlled conveying device (20) and on which several thin sections of tissue (2b) are placed on small metal screens (2) is immersed like a die into a liquid that is composed of a washing or marking solution (6) and is placed in several recesses (5) within an object support (4). The object support can also be automatically moved.

33 Claims, 4 Drawing Sheets

U.S. PATENT DOCUMENTS

| | | | |
|---|---|---|---|
| 4,911,098 A | | 3/1990 | Tabata |
| 5,839,091 A | * | 11/1998 | Rhett et al. ............... 702/19 |
| 5,985,214 A | * | 11/1999 | Stylli et al. ............... 422/65 |
| 6,103,518 A | * | 8/2000 | Leighton ............... 435/286.3 |
| 6,330,106 B1 | | 12/2001 | Greenwald et al. |
| 6,534,008 B1 | | 3/2003 | Angros |
| 6,746,851 B1 | * | 6/2004 | Tseung et al. ............. 435/40.5 |
| 2002/0114733 A1 | | 8/2002 | Copeland et al. |

FOREIGN PATENT DOCUMENTS

| | | |
|---|---|---|
| EP | 323130 A2 * | 7/1989 |
| WO | WO 200104634 A1 * | 1/2001 |

\* cited by examiner

DEVICE AND METHOD FOR CARRYING OUT IMMUNOLOGICAL MARKING TECHNIQUES FOR THIN-SECTIONED TISSUE

TECHNICAL FIELD

The present invention concerns a device for treating thin-sectioned tissue on a support plate with at least one treatment liquid. Moreover, the present invention concerns a method for treating thin-sectioned tissue on a support plate with at least one treatment liquid.

BACKGROUND OF THE INVENTION

To be able to study the structure of biological specimens such as tissues or cells with an electron microscope, ultra-thin sections only a few nm in size are prepared and placed on object support screens made of metal, preferably of nickel (in the following referred to as small metal screens). For electron-microscopic studies, the sections are rendered contrasty or individual constituents of the specimen are marked by use of special or cytochemical methods. These cytochemical methods are often based on the principle of ligand pair formation, the first ligand possibly being present in the biological specimen and the second ligand, upon coming in contact with this specimen, binding as binding partner to the first ligand. Examples of biologically based ligand pairs are antigen/antibody binding pairs, enzyme/substrate binding pairs, lecithin/sugar, hormone/receptor systems, DNA/DNA pairs and DNA/RNA pairs.

The prior art discloses numerous methods involving the antigen/antibody binding pair. These methods are collectively referred to as immunohistochemistry and immunocytochemistry (in the following referred to as marking techniques). For example, U.S. Pat. No. 5,143,714 discloses a method whereby an antigen is adsorbed from a liquid specimen into a pelletizable gel substance. The gel pellet is surrounded by a diffusion barrier, integrated as a block into a punched-out gel matrix and subsequently, as a tissues specimen, subjected to immunological marking techniques. DE 38 78 167 T2 describes the use of colloidal gold particles for the marking of ligands by the immunogold staining technique. A greatly improved method permitting qualitative and quantitative evaluation of an antigen in a specimen is disclosed in U.S. Pat. No. 5,079,172 as a sandwich assay whereby the antigen-binding first antibody is marked with a gold-labeled second antibody that binds to the first antibody. By the electron-microscopic evaluation method, the antigen in the specimen can be determined qualitatively and quantitatively from the amount of gold particles.

Many procedures of immunohistochemistry and immunocytochemistry for immunological marking of thin-sectioned tissues have in common the feature that in most cases they consist of 10 to 20 individual processing steps. In a large number of cases, the processing steps consist of washing the specimen to be studied with buffering or marking solutions.

Such washing is currently carried out manually by an expensive procedure whereby individual drops of the aqueous buffer solution or marking solution are placed onto a hydrophobic substrate (for example PARAFILM®, PARLODION®, Colloidion or FORMFAN®). The small metal screens with the thin-sectioned tissue are placed individually onto the drops to enable the tissue to react with the treatment liquid. Because of the light weight of the small metal net and the surface tension of the liquid drop, the small metal net floats on the surface of the drop. After a certain contact time for this step (often 5–10 min), the small metal net is moved on to the next drop by use of tweezers. This is continued all the way to the last position of the standard procedure tying down an operator for up to several hours per immunological marking reaction.

It can readily be seen that this manual process requires the continuous attention of the working personnel and that the labor costs are high because of the large amount of time involved. The number of specimens that can be worked on at the same time is very limited, and errors by the working personnel during the exact pipetting and positioning of liquid drops of very small volume cannot be excluded. The manual method cannot exclude mixing up the specimens after the long treatment period during the immunological marking, but this could be prevented by use of a specimen carrier with identification in the form of a chip or bar code, as described in Utility Model DE 299 06 382 U1.

Furthermore, the evaporation of the liquid drops during prolonged standard procedures presents a major problem.

Although Utility Model DE 298 17 912 U1 discloses a device for washing preparations to be subjected to microscopy on carriers following immunochemical treatment, this device is a washing box in which a major quantity of washing solution flows over the preparation and the carrier at a certain flow rate. Such a device is not suited for immunological marking techniques, because the antibody-containing marking solutions used are very expensive, and hence, are used in only very small volumes. To date, no device or method is known that allows an automated execution of immunological marking techniques for thin-sectioned tissues.

SUMMARY OF THE INVENTION

The object of the invention is therefore to provide a suitable device for the treatment of thin-sectioned tissues that makes it possible to process several thin-sectioned tissues effectively, nearly automatically and in time-saving and reproducible manner.

This objective is reached by means of a device for treating thin-sectioned tissues on a support plate with at least one treatment liquid, wherein the support plate is disposed opposite an object support in a treatment position, and that several object supports can be automatically placed into this treatment position.

Another object of the invention is a method for treating thin-sectioned tissues for the purpose of carrying out immunological marking techniques and that makes it possible to process several thin-sectioned tissues effectively, nearly automatically and in time-saving and reproducible manner.

According to the invention, this objective is reached by means of a method which comprises treating thin-sectioned tissues on a support plate with at least one treatment liquid by the steps of filling at least one object support on which are present recesses with a treatment liquid; bringing the object support into a treatment position; lowering the support plate onto the object support to bring about contact between the treatment liquid and the thin-sectioned tissues, and automatically moving the object support to the next treatment position.

The device according to the invention consists essentially of two parts: a support plate on which small metal screens are placed and held with a magnet, and an object support provided with recesses (known as wells) that can be filled with at least one liquid (treatment liquids for immunological marking or washing solutions, both known from the prior art). The positions of the recesses correspond in their arrangement to the positions of oppositely located small metal screens on the support plate. In one arrangement, both parts of the device can be introduced into a conveying device with controllable raising and lowering function in a manner such that the support plate with the small metal screens comes in contact with the liquid drop in the recesses of the object support from above, like a die. This procedure permits automatization of immunological marking methods for thin-sectioned tissues intended for electron-microscopic studies. Several object supports can be automatically assigned to a treatment position, and a multiplicity of small metal screens can be disposed on a single support plate, so that the number of specimens that are to be worked on simultaneously is markedly increased. The device for treating thin-sectioned tissues contains at least one support plate so that the thin-sectioned tissues can be treated with at least one treatment liquid. At least one object support in a treatment position is disposed opposite the support plate. Several object supports can be brought automatically into this treatment position. The support plate defines an underside on which the marked positions are indicated and where small metal screens with thin-sectioned tissues are positioned. The support plate also defines an upper side containing several holes each hole containing a wedged-in magnet. The holes are disposed opposite the marked positions. The object support defines an upper side containing free recesses configured for receiving the treatment liquid.

BRIEF DESCRIPTION OF THE DRAWINGS

In the following, the invention will be explained by reference to the examples that are schematically represented in the drawings, in which.

DESCRIPTION OF THE PREFERRED EMBODIMENTS

Figure 1:
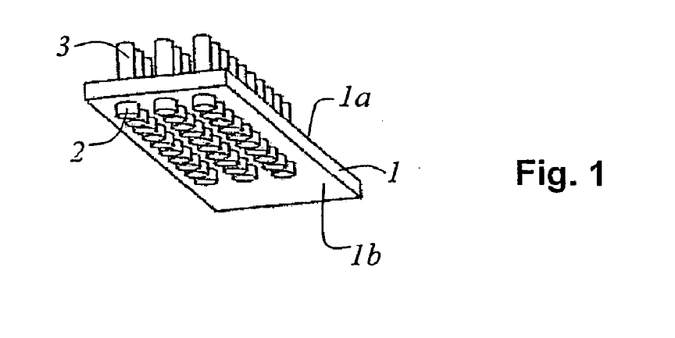
FIG. 1 is a view in perspective of a support plate carrying small metal screens.

FIG. 1 shows a support plate 1 of the invention that defines an upper side 1*a* and an underside 1*b*. On underside 1*b*, support plate 1 is provided with marked positions on which are located small metal screens 2 with the thin-sectioned tissues (not shown here). Preferably, the positions of the small metal screens 2 on the support plate 1 are raised. This prevents the formation of liquid bridges between the individual small metal screens 2 when said screens make contact with the liquid drops. On the upper side 1*a* of support plate 1 are located, opposite the positions of small metal screens 2, holes 3*a* (see FIG. 3) in which are lodged magnets 3, for example, permanent magnets. Said magnets keep small metal screens 2 in their place on the underside 1*b* of support plate 1 by magnetic force. The distance between small metal screens 2 and magnet 3 should be as small as possible (distance<2 mm). Support plate 1 preferably consists of dimensionally stable non-magnetic material, preferably aluminum, brass or a fiber-reinforced plastic material, and underside 1*b* is advantageously provided with a hydrophobic coating (for example, a TEFLON® compressive coating]. To a person skilled in the art, it is self-evident that numerous embodiments are possible for the shape of support plate 1 and for the arrangement of the small metal screens 2 on support plate 1. In the embodiment represented here, three small metal screens 2 are located on a rectangular plate with dimensions of about 76×26 mm (3×1 inch; object support size), said small metal screens having a diameter of 3 mm. It is critical that the positions of small metal screens 2 on the underside 1*b* of support plate 1 be located opposite the holes for magnets 3 on upper side 1*a* of support plate 1, and preferably, also opposite the positions of at least one liquid drop 6 on upper side 4*a* of an object support 4 (see FIG. 2).

In another embodiment, small metal screens 2 are held on the underside 1*b* of support plate 1 by electromagnets (not shown).

Figure 2:
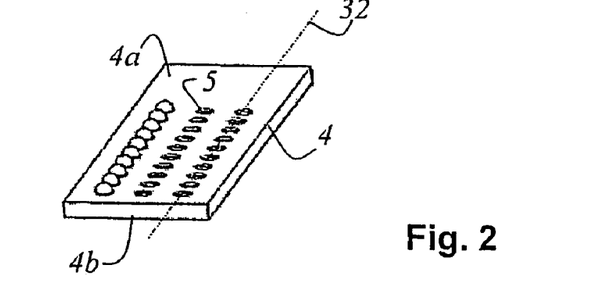
FIG. 2 is a view in perspective of an object support with recesses that can be filled with at least one treatment liquid.

FIG. 2 shows a view in perspective of the object support 4 of the invention that defines an upper side 4*a* and an underside 4*b*. On upper side 4*a*, object support 4 is provided with several recesses 5 (known as wells) which in the embodiment shown are arranged in a line and each is filled with a liquid drop 6. Liquid drop 6 consists of a washing solution or a treatment solution as disclosed in the prior art. It is also possible for individual recesses 5 to contain different liquids (for example one line of recesses 5 filled with washing solution, the next line of recesses 5 filled with marking solution). Advantageously, object support 4 is transparent and is made of dimensionally stable material. Object support 4 is preferably made of glass or a plastic material, the upper side 4*a* of said support that carries recesses 5 and the recesses 5 themselves being covered with a hydrophobic coating (for example, with a Teflon® compressive coating 5*a*). Recess 5 is identical with thickness D (see FIG. 3) of the Teflon coating 5*a*. Recess 5 preferably amounts to about 50 μm. Recesses 5 hold a liquid volume which for washing solution is about 50 μL and for antibodies and gold solutions about 5 μL. The Teflon compressive coating is the same for different drop sizes. Because of the hydrophobic boundary layer, the liquid drops 6 are more or less curved upward. To bring the small screens in contact with these drops, it is absolutely necessary for the operation that one know the drop size, because a difference in drop size will require a different position for the lowering movement of small metal screens 2.

Figure 3:
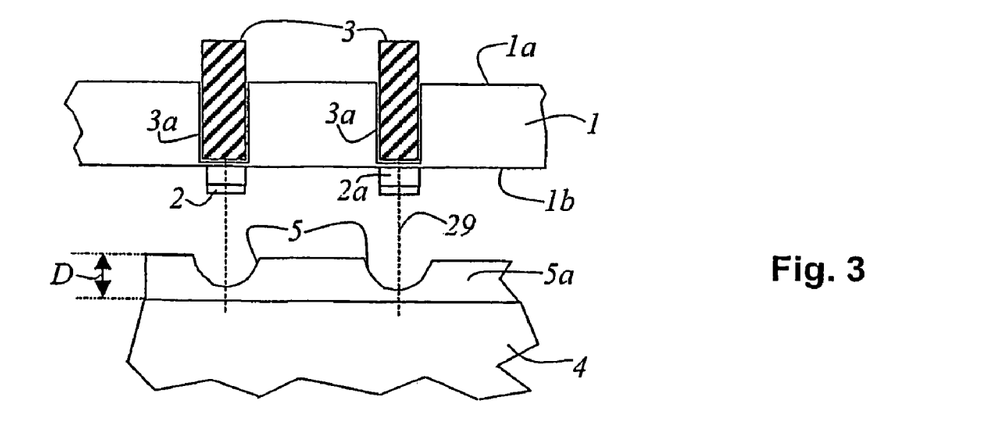
FIG. 3 is a detailed cross-sectional view of the support plate and object support.
Figure 4:
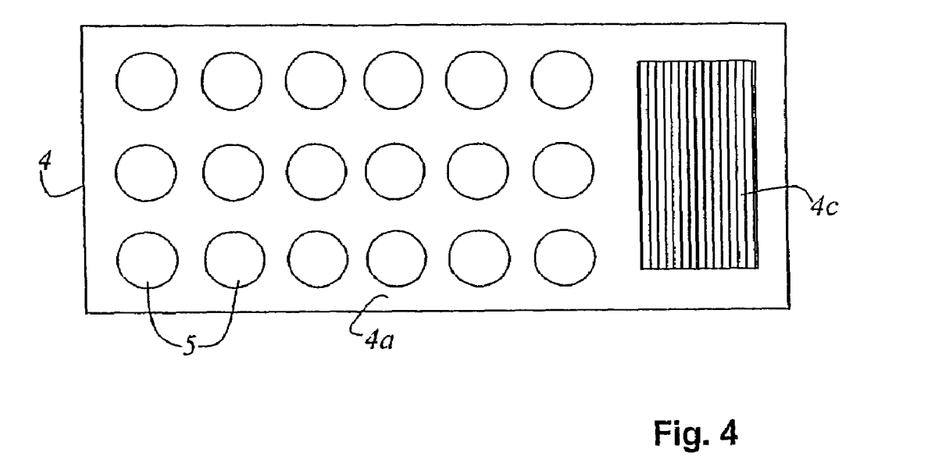
FIG. 4 is a top view of one embodiment of the object support.

FIG. 3 shows a partial cross-sectional view of the relative spatial relationship of object support 4 to support plate 1. The partial view of the cross-section is defined, for example, in FIG. 2 by broken line 32. In the embodiment shown here, object support 4 has applied to it a hydrophobic coating 5*a* having thickness D. In support plate 1, there are provided holes 3*a* for magnets 3. On the underside 1*b* of support plate 1 are present marked positions 2*a* each of which carries one small metal net 2. Small metal net 2 is held by magnets 3 assigned to marked positions 2*a*. The dash-and-dot line 29 in FIG. 3 shows clearly that support plate 1 and object support 4 are disposed in a manner such that one marked position 2*a* with a small metal net 2 is located opposite a recess 5, FIG. 4 shows a top view of object support 4. This is a further embodiment of object support 4. For identification, object support 4 is advantageously provided with an identification as described, for example, in Utility Model DE 299 06 382 U1. Identification 4c is located on surface 4a of object support 4 and can be in the form of a bar code or a chip. To a person skilled in the art it will be obvious that numerous embodiments are possible for the size and shape of object support 4 as well as for the arrangement of recesses 5 on upper side 4a of object support 4. On a rectangular surface with dimensions of 76 mm×26 mm, there can be disposed, for example, 10×3 recesses 5 with a size from 2 mm to 3 mm. It is critical that the positions of liquid drops 6 on upper side 4a of object support 4 be disposed opposite the positions of small metal screens 2 on the underside 1a of support plate 1 (see representation in FIG. 3).

Figure 5:
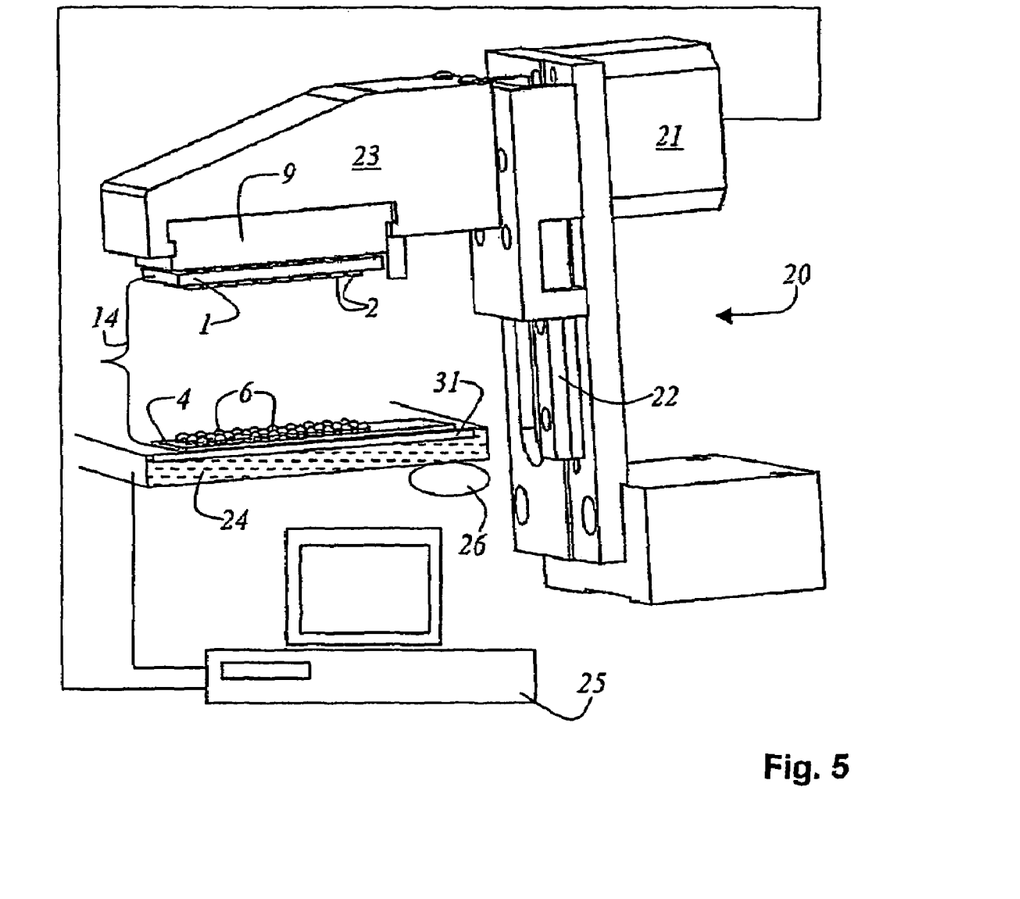
FIG. 5 is a view in perspective of the conveying device for placing the support plate onto the object support.

FIG. 5 shows support plate 1 of the invention in a conveying device 20 with controllable raising and lowering function. Conveying device 20 is designed so that several object supports 4 can successively be brought in contact with support plate 1. Conveying device 20 is controlled so that the positions of recesses 5 of object support 4 containing liquid drops 6 are located exactly opposite the positions of small metal screens 2 on the underside 1b of support plate 1. To this end, by means of a motor 21 of conveying device 20, support plate 1 is centered from above, parallel and sideways, until the positions of small metal screens 2 and those of liquid drops 6 are located exactly opposite each other. Conveying device 20 then brings support plate 1 closer to object support 4. For this purpose, on conveying device 20 there is provided a track 22 that lowers support plate 1 linearly onto object support 4, said support plate being held by means of a holder 9 in a holding head 23 of conveying device 20. Object supports 4 are placed, for example, on a conveyor 24 that moves the object supports 4 in an appropriate manner toward conveying device 20. Conveying device 20 and conveyor 24 are controlled and guided by a computer unit 25 and an appropriate computer program.

Figure 6:
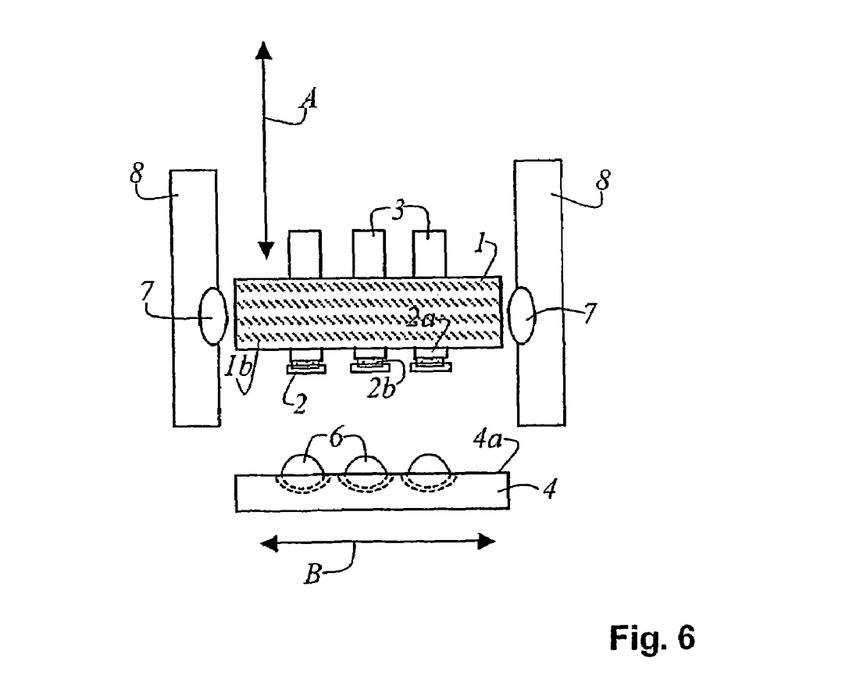
FIG. 6 is a schematic representation of the support plate which with the aid of the conveying device is in approximate contact with an object support.

FIG. 6 shows a schematic representation of the support plate 1 of the invention which by conveying device 20 (see FIG. 5) is brought into approximate contact with object support 4. On its underside 1b, support plate 1 is provided with marked positions 2a at which are located in raised position small metal screens 2 with thin-sectioned tissues 2b. On upper side 1a of support plate 1 are located opposite the positions of small metal screens 2 holes 3a in which are lodged magnets 3 so as to keep small metal screens 2 in their place on underside 1b of support plate 1 by magnetic force.

At a certain small distance between underside 1b of support plate 1 and the upper side 4a of object support 4, liquid drops 6 wet the thin-sectioned tissues 2b on small metal screens 2. This distance depends on the volume of liquid drop 6 and varies from 0.5 mm to 4 mm. The transport of support plate 1 and object support 4 is accomplished by linear guidance provided by a stepping motor (not shown). The positions of object support 4 and support plate 1 are monitored by position sensors 7 and correspondingly controlled. The signals from the various position sensors 7 are used for control purposes. In the embodiment shown here, there are provided vertical, parallel guidance tracks 8 by means of which holding head 23 (see FIG. 5) together with support plate 1 that is fixed in a holder 9 can be lowered onto object support 4. Holder 30 fixes support plate 1 and one object support 4 relative to each other in a treatment position 14 (see FIG. 5). In this case, small metal screens 2 carrying a thin-sectioned tissue 2b are in contact with liquid drops 6 on the upper side 4a of object support 4. After a preset incubation time, a change of support plate 1 to the next arrangement of liquid drops 6 on the same object support 4 or on the next object support 4 is brought about automatically. To this end, support plate 1 is automatically lifted, and object support 4 is transported one position further. Arrow A in FIG. 6 indicates the vertical transport direction of support plate 1, while arrow B shows the horizontal transport direction of object support 4.

The subsequent course of the transport of object support 4 is not described in detail, but it can occur in various ways. Those skilled in the art know, for example, the following arrangements: Object supports 4 are placed on a linear conveyor 24 moved by a motor 26. Alternatively, object supports 4 are placed on a circular conveyor 24 also moved by a motor.

To prevent a reduction in volume of liquid drops 6 by evaporation, object supports 4 on conveyor 24 are provided with a cover 10 so as to form a chamber 11. In this chamber 11, high air humidity is attained, for example, by inserting moist filter paper 13 on a holder 12, the evaporation of liquid drops 6 thus being minimized.

Figure 7:
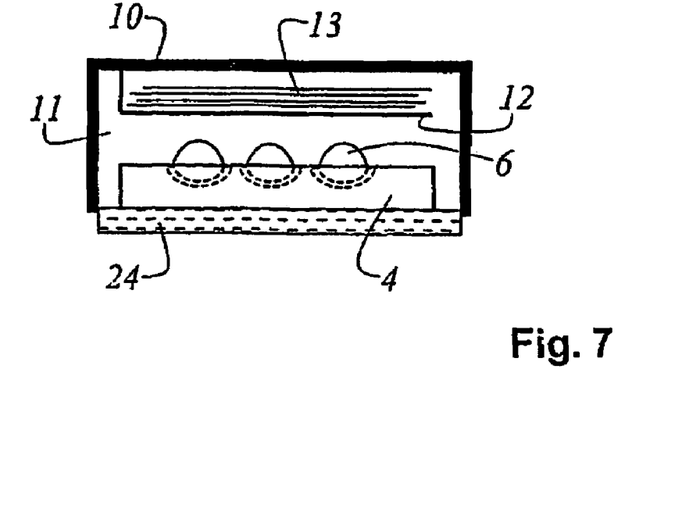
FIG. 7 is a schematic representation of the chamber for protection against evaporation of the liquid drops on the object supports.

FIG. 7 shows a schematic representation of chamber 11 as evaporation protection for liquid drops 6 on object support 4. In the chamber, a stack of moist absorbent paper 13 is held on a holder 12. Before liquid drops 6 come in contact with small metal screens 2, cover 10 is automatically opened, at least partly.

Figure 8:
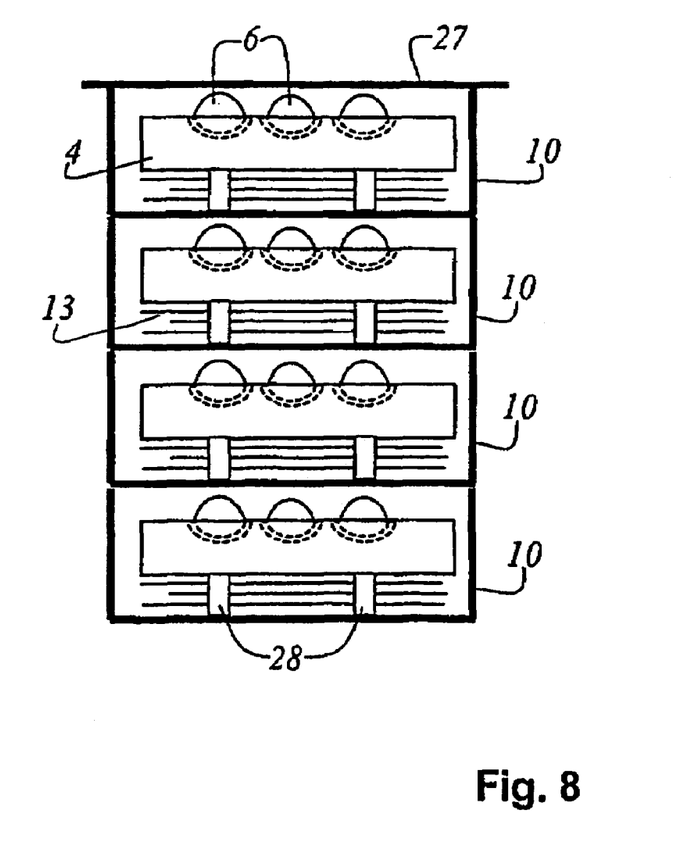
FIG. 8 is a schematic representation of another embodiment of the chamber for protection against evaporation of the liquid drops on the object support.

FIG. 8 shows a schematic representation of another embodiment of chamber 11 as evaporation protection for liquid drops 6 on object support 4. In a different embodiment, chamber 4 is designed, for example, so that the moist filter paper 13 is located in chamber 11 below object support 4. In this embodiment, several chambers 11 are stacked one on top of another, the next chamber being placed on the chamber below it thus closing it. The moisture of filter paper 13 passes by object support 4 from below and laterally and then enters chamber 11. Object support, so to speak, thus rests on stilts 28 in a pool. The top-most chamber 11 is finally closed off with a cover 27. Object supports 4 are transported to treatment position 14 in an appropriate manner. In the treatment position, support plate 1 is brought in contact with the object support.

The device of the invention is so configured that it carries out automatically the following steps of an already existing standard procedure for immunological marking of thin-sectioned tissues: saturating non-specific bonds, antibody incubation and diverse washing steps with different washing solutions.

In another embodiment, in the treatment position there is provided a heat source, for example in the form of a small electric resistance device, or a cooling unit, for the purpose of adjusting the optimum reaction temperature of object support 4 and liquid drops 6. Said heat source is configured so that an electric contact of the object carrier triggers the heating or cooling device of said object support. The heat source or cooling unit is controlled by means of temperature sensors disposed on object support 4 or in the vicinity of the liquid drop and is regulated by the attached computer unit 25 and an appropriate computer program. The heating or cooling of object supports 4 can also occur by contact of object supports 4 with a temperature-regulated metallic plate 31.

A further object of the invention is a method whereby, by use of the described device, several small metal screens 2 with thin-sectioned tissues 2b resting thereon are treated on a support plate 1, particularly to carry out immunological marking and/or washing steps reproducibly, at the same time, effectively and in time-saving manner. The automated procedure reduces the human source of error.

The method optimizes the treatment, particularly the carrying out of immunological marking and/or washing steps for thin-sectioned tissues for electron-microscopic specimens. The individual procedures concerning the kind of liquid and incubation time can be found in the prior art.

Instead of transporting small metal screens 2 with tweezers from one liquid drop 6 to the next one, thin-sectioned tissues 2b are positioned on small metal screens 2 and placed on support plate 1 of the invention which is provided with marked and raised positions 2a and to the underside 1b of which has advantageously been applied a hydrophobic coating. Magnets 3 located on the upper side 1a of support plate 1 hold the small metal screens 2 in their place by magnetic force (see FIG. 6).

Support plate 1 is held by a conveying device 20 with controllable raising and lowering function (see FIG. 5) and lowered.

With a microliter pipette, liquid drops 6 of an exact volume are placed into recesses 5 of object support 4 of the invention. In the treatment position 14, the positions of the liquid drops 6 on object support 4 are located exactly opposite the positions of small metal screens 2 on support plate 1 (see FIG. 6).

Object support 4 is placed on conveyor 24 of conveying device 20. The adjustment of the object support 4 and of liquid drops 6 to a certain temperature is done by means of computer unit 25 through a heat source or cooling unit (not shown) which are triggered by an electric contact of the object support.

Conveying device 20 and conveyor 24 cooperate with one another in that support plate 1 with small metal screens 2 is centered parallel to and laterally relative to object support 4. The positions of small metal screens 2 and of liquid drops 6 are located exactly opposite each other. Cover 10 which protects liquid drops 6 from evaporation and attendant volume reduction in a chamber 11 with moist absorbent paper 13 is automatically at least partly opened. At a certain small distance between support plate 1 and object support 4, liquid drops 6 wet the small metal screens 2. This position is now held constant for the particular programmed incubation time. The distance depends on the drop volume and varies from 0.5 mm to 4 mm. The motor driven transport mechanisms of conveyor 24 and conveying device 20 are controlled by computer unit 25, a computer program and position sensors 7.

At the end of the selected incubation time, support plate 1 automatically moves over to the next liquid drop 6. Support plate 1 is automatically lifted by use of conveying device 20 and sensor 7, and object support 4 is automatically transported further by one position, or an object support 4 with liquid drops 6 is automatically introduced into a carousel, a cartridge or a stack from a linear guide with several object supports.

By this method, the following steps of a standard procedure for immunological marking of thin-sectioned tissues from the prior art with several small metal screens 2 and thin-sectioned tissues 2b resting thereon are carried out automatically and reproducibly: saturation of non-specific bonds, antibody incubation and diverse washing steps with different washing solutions.

The invention was described by reference to a particular embodiment. It will be obvious to a person skilled in the art, however, that derivations and modifications thereof can be performed without exceeding the protective scope of the claims.

LIST OF REFERENCE NUMERALS

1 Support plate
1a Upper side of support plate
1b Underside of support plate
2 Small metal screens
2a Marked positions on support plate
2b Thin-sectioned tissue
3 Magnets
3a Holes for magnets
4 Object support
4a Upper side of object support
4b Underside of object support
4c Identification on object support
5 Recesses (wells)
5a Teflon coating
6 Liquid drops
7 Position sensors
8 Vertical guiding tracks of conveying device
9 Holder for support plate
10 Cover of object support
11 Chamber
12 Holder for absorbent paper
13 Stack of moist absorbent paper
14 Treatment position
20 Conveying device
21 Motor of conveying device
22 Guiding track of conveying device
23 Holding head
24 Conveyor
25 Computer unit
26 Motor of conveyor
27 Cover
28 Stilts
29 Dash-dot line
30 Holder for conveying device
31 Temperature-regulated plate
32 Broken line
A Arrow indicating vertical transport direction
B Arrow indicating horizontal transport direction
D Thickness

I claim:

1. A device for treating thin-sectioned tissues with at least one treatment liquid, said device comprising a support plate for said tissues and an object support comprising recesses for said at least one treatment liquid, said support plate disposed opposite said object support when in a treatment position and comprises an upper side and an underside with marked positions and metal screens for mounting said thin-sectioned tissues, said upper side having a plurality of magnets disposed in holes, said holes being positioned opposite said marked positions, wherein said device is adapted so that a plurality of said object supports can be automatically placed into said treatment position.

2. The device according to claim 1, wherein said marked positions for said metal screens are formed as elevations on the underside of the support plate.

3. The device according to claim 1, wherein said magnets in the holes on the upper side of the support plate are permanent magnets or electromagnets.

4. The device according to claim 1, wherein said support plate is comprised of a dimensionally stable material.

5. The device according to claim 1, wherein said support plate is treated with a hydrophobic coating on the underside carrying said metal screens.

6. The device according to claim 1, wherein said object support comprises an upper side with recesses for containment of said treatment liquid, said recesses positioned opposite said metal screens.

7. The device according to claim 1, further comprising means for holding said support plate and conveying means with motor means for raising and lowering said support plate.

8. The device according to claim 7, further comprising computer means and position sensors for automatic control of said conveying means.

9. The device according to claim 1, wherein said object support comprises an upper side with free recesses adapted for receiving the treatment liquid.

10. The device according to claim 9, wherein said object support is comprised of a transparent, dimensionally stable material selected from the group consisting of glass and a fiber-reinforced plastic.

11. The device according to claim 9, wherein said object support comprises a hydrophobic coating on the upper side containing the recesses.

12. The device according to claim 11, wherein the depth of the recesses on the upper side of the object support is about the same as the thickness of the hydrophobic coating.

13. The device according to claim 9, wherein a liquid volume of the recesses of the object support is at least 5 µL.

14. The device according to claim 9, wherein the treatment liquid is a marking and/or washing solution for carrying out immunological marking techniques for thin-sectioned tissues.

15. The device according to claim 9, wherein said object support further comprises a bar code and/or chip for data storage.

16. The device according to claim 9, wherein the recesses for the treatment liquid on the upper side of the object support are arranged opposite the positions of the metal screens on the underside of the support plate.

17. The device according to claim 9, further comprising conveyor means for transmission of said object support, a guiding track and a motor, said guiding track and motor providing means for establishing said treatment position.

18. The device according to claim 17, further comprising computer means and position sensor means for automatically controlling said conveyor.

19. The device according to claim 17, wherein on said conveyor said object support is provided with cover means so as to form a chamber therefor, said device including means for at least partially opening said cover means automatically.

20. The device according to claim 19, wherein said chamber further comprises means for holding an absorbent for elevated humidity in said chamber for minimizing evaporation of the treatment liquid on the object supports.

21. A method for treating thin-sectioned tissues on a support plate with at least one treatment liquid by the steps which comprise:
(i) filling at least one object support comprising recesses with said at least one treatment liquid;
(ii) mounting said thin-sectioned tissues on metal screens resting on marked and raised positions on the underside of said support plate maintained in place by magnetic means disposed in holes on the upper side of said support plate opposite said marked positions;
(iii) bringing the object support into a treatment position;
(iv) lowering the support plate onto the object support for contact between the treatment liquid and the thin-sectioned tissues, and
(v) at least automatically moving the object support to a next treatment position.

22. The method according to claim 21, wherein the treatment of the thin-sectioned tissues comprises immunological marking and/or washing steps.

23. The method according to claim 21, wherein the treatment of the thin-sectioned tissues is carried out automatically.

24. The method according to claim 21, including the step of holding the support plate by fastening to a holding head of a conveying device with automatic raising and lowering functionalities.

25. The method according to claim 21, including the step of filling said recesses with a marking and/or washing solution for performing immunological marking techniques for thin-sectioned tissues.

26. The method according to claim 21, comprising the step of bringing the object support into a treatment position so that the treatment liquid in the recesses of the object support is located opposite the thin-sectioned tissues on the metal screens of the support plate.

27. The method according to claim 21, comprising the step of transporting said object support to said treatment position by means of a conveyor with the aid of a guiding track and motor.

28. The method according to claim 27, including the step of controlling said conveyor with the aid of a computer and position sensors.

29. The method according to claim 28, including the step adjusting said conveyor so the support plate is brought in close proximity to the object support, wherein the thin-sectioned tissues on the metal screens come in contact with the treatment liquid on the object support.

30. The method according to claim 21, including the step of at least partially automatically opening a chamber for the liquid on said object support before contact occurs between the thin-sectioned tissues on the support plate and the treatment liquid.

31. The method according to claim 21, comprising the step of contacting said thin-sectioned tissues on the support plate with the treatment liquid on the object support over any desired incubation period.

32. The method according to claim 31, comprising the step of automatically lifting said support plate at the end of the incubation period along guiding tracks, wherein the object support on the conveyor is automatically brought into another treatment position.

33. The method according to claim 21, wherein the object support comprises an upper side containing free recesses configured for receiving the treatment liquid.

* * * * *